(12) United States Patent
Kim et al.

(10) Patent No.: US 7,892,761 B2
(45) Date of Patent: Feb. 22, 2011

(54) PROTEIN MARKERS FOR DIAGNOSING STOMACH CANCER AND THE DIAGNOSTIC KIT USING THEM

(75) Inventors: Chul Woo Kim, Guri-si (KR); Syng-Yup Ohn, Seoul (KR); Mi Young Han, Seoul (KR); Yong-Sung Shin, Seoul (KR)

(73) Assignee: Bioinfra Inc. (KR)

( * ) Notice: Subject to any disclaimer, the term of this patent is extended or adjusted under 35 U.S.C. 154(b) by 149 days.

(21) Appl. No.: 12/281,086

(22) PCT Filed: Dec. 28, 2006

(86) PCT No.: PCT/KR2006/005836
§ 371 (c)(1),
(2), (4) Date: Aug. 28, 2008

(87) PCT Pub. No.: WO2007/100183
PCT Pub. Date: Sep. 7, 2007

(65) Prior Publication Data
US 2009/0018026 A1    Jan. 15, 2009

(30) Foreign Application Priority Data
Feb. 28, 2006 (KR) .................. 10-2006-0019517

(51) Int. Cl.
*G01N 33/53* (2006.01)
(52) U.S. Cl. ...................................... 435/7.1
(58) Field of Classification Search ........ None
See application file for complete search history.

(56) References Cited

U.S. PATENT DOCUMENTS

2004/0121343 A1    6/2004 Buechler et al.

2005/0064516 A1 *  3/2005 Kantor et al. ............... 435/7.1

FOREIGN PATENT DOCUMENTS

EP    1394182    3/2004

OTHER PUBLICATIONS

Ryu (J. Korean Med Sci, 2003, 18:505-509).*
Tockman et al (Cancer Res., 1992, 52:2711s-2718s).*
Kawakami et al (Proteomics, 2005, 5:4287-4295).*
QY He and JF Chiu, "Proteomics in biomarker discovery and drug development", J. Cell Biochem. Aug. 2003 vol. 89(5), pp. 868-886.
QY He, et al., "Diverse proteomic alterations in gastric adenocarcinoma", Proteomics Oct. 2004 vol. 4(10), pp. 3276-3287.
JS Jang, et al., "The differential proteome profile of stomach cancer: identification of the biomarker candidates", Oncol. Res. 2004 vol. 14(10), pp. 491-499.
J.S. Kim, "Identification of a possible marker protein for gastric cancer by proteomic analysis", Master Thesis of College of Pharmacy, Choong-Ang University (Korea), 2002.
J.W. Ryu, et al., "The proteomics approach to find biomarkers in gastric cancer", J. Korean Med. Sci. 2003 vol. 18, pp. 505-509.

* cited by examiner

*Primary Examiner*—Sean E Aeder
(74) *Attorney, Agent, or Firm*—Klarquist Sparkman, LLP

(57) ABSTRACT

The present invention relates to protein markers for diagnosing stomach cancer and a diagnostic kit using the same, more precisely protein markers screened by two-dimensional gel electrophoresis and bioinformatics and a diagnostic kit using the same. The markers of the invention can be effectively used for diagnosing stomach cancer and evaluating the extent of progress of the cancer by confirming the expression levels of those marker proteins whose expressions differ in stomach cancer patients from in normal healthy people.

7 Claims, 4 Drawing Sheets

[Fig. 1]
1
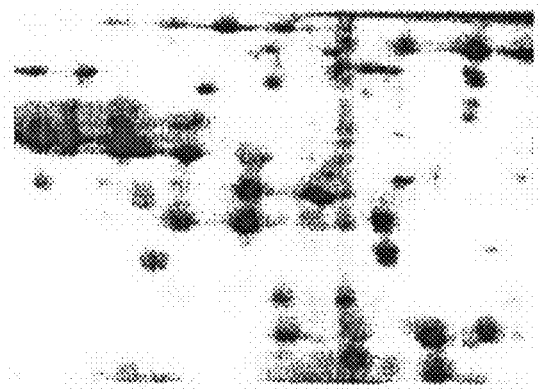
2
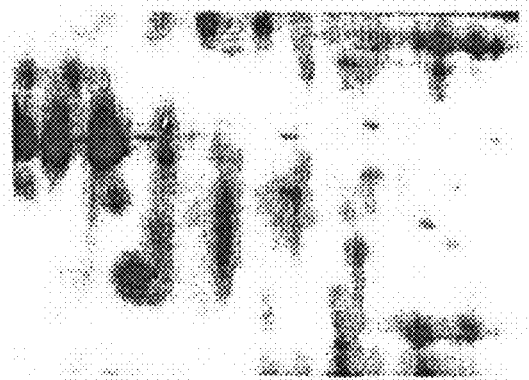
3

[Fig. 2]
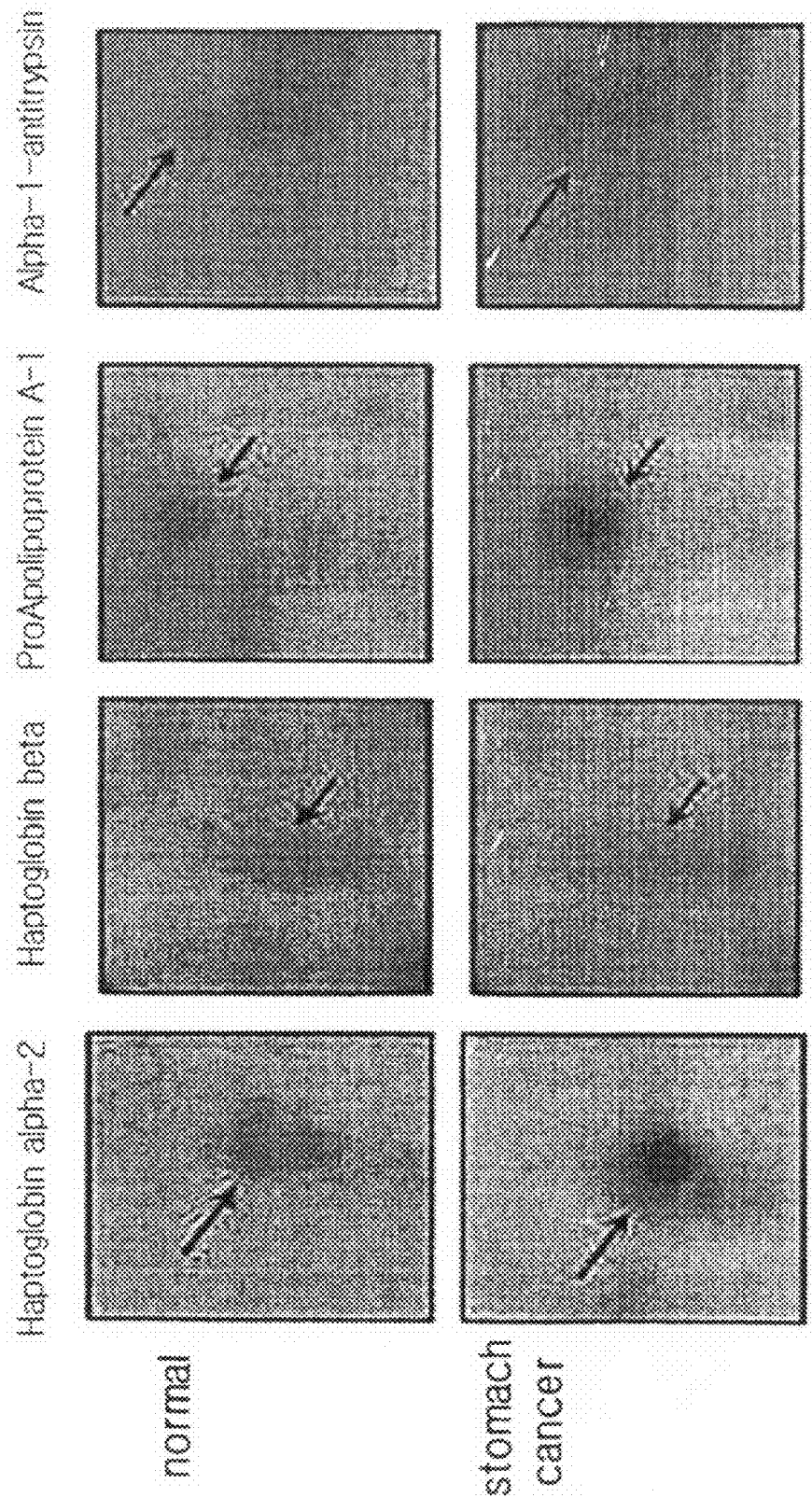

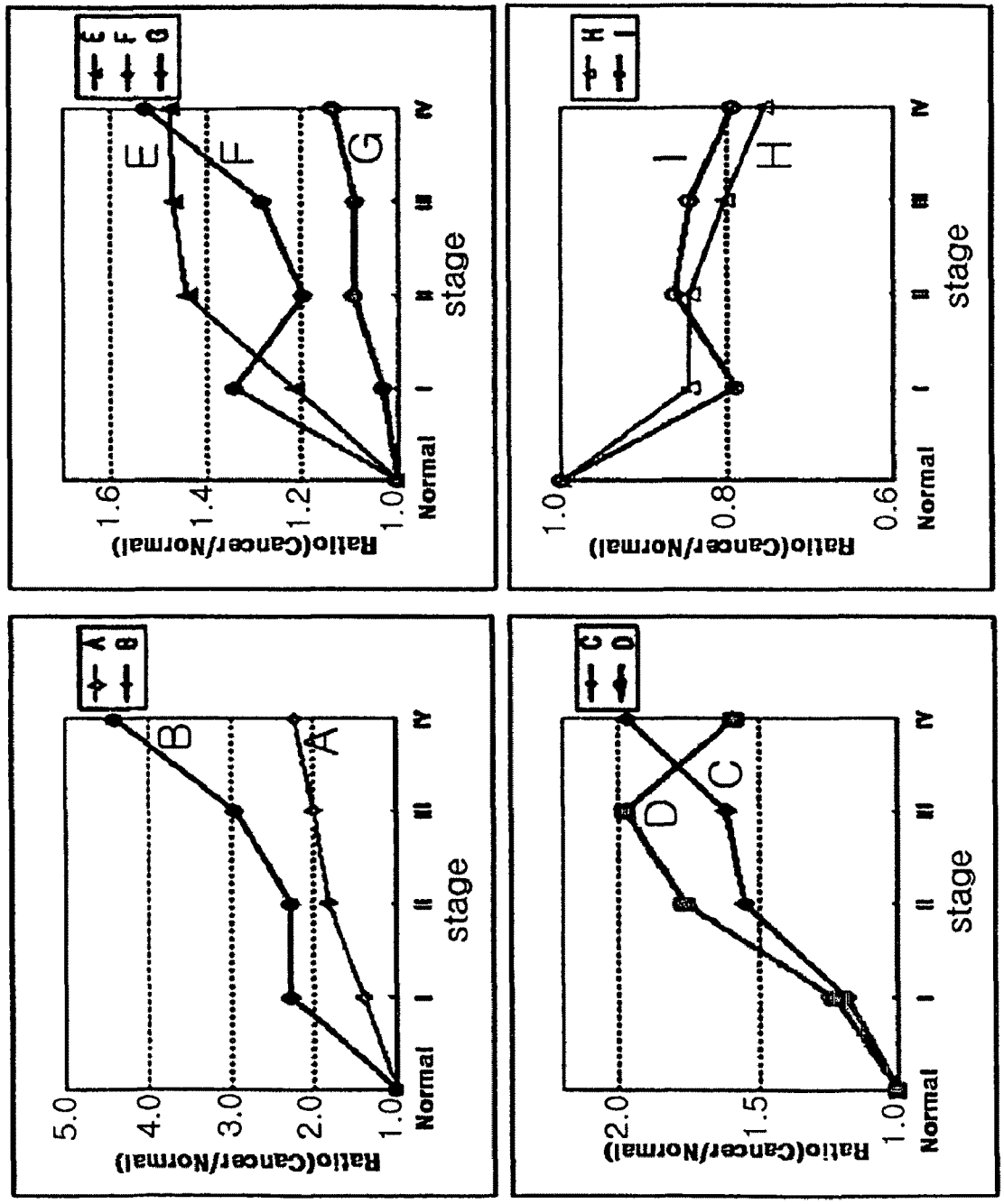
[Fig. 3]

[Fig. 4]
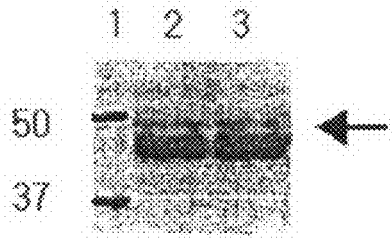
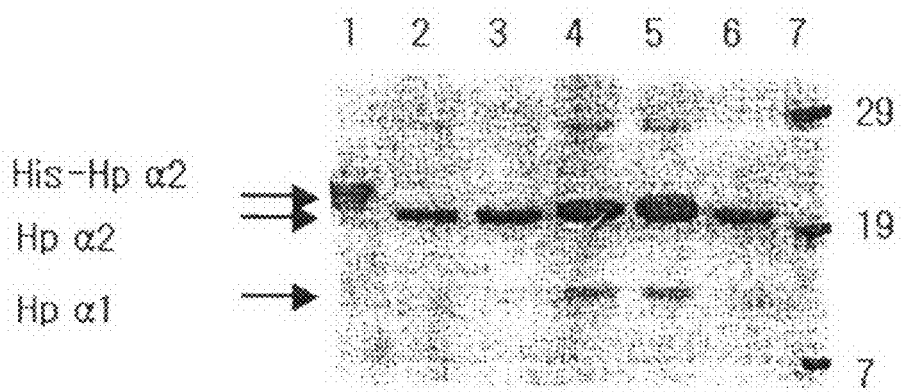
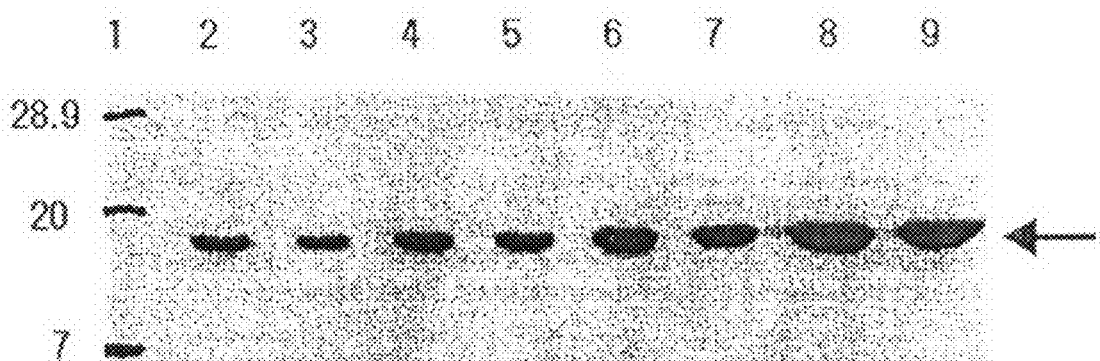
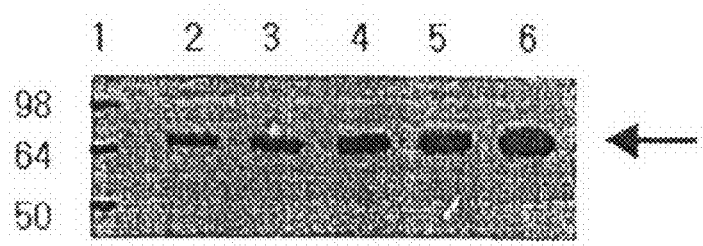

```
                        SEQUENCE LISTING

<160> NUMBER OF SEQ ID NOS: 9

<210> SEQ ID NO 1
<211> LENGTH: 312
<212> TYPE: PRT
<213> ORGANISM: Homo sapiens

<400> SEQUENCE: 1

Val Thr Leu Ser Pro Lys Asp Cys Gln Val Phe Arg Ser Asp His Gly
1               5                   10                  15

Ser Ser Ile Ser Cys Gln Pro Pro Ala Glu Ile Pro Gly Tyr Leu Pro
            20                  25                  30

Ala Asp Thr Val His Leu Ala Val Glu Phe Phe Asn Leu Thr His Leu
        35                  40                  45

Pro Ala Asn Leu Leu Gln Gly Ala Ser Lys Leu Gln Glu Leu His Leu
    50                  55                  60

Ser Ser Asn Gly Leu Glu Ser Leu Ser Pro Glu Phe Leu Arg Pro Val
65                  70                  75                  80

Pro Gln Leu Arg Val Leu Asp Leu Thr Arg Asn Ala Leu Thr Gly Leu
                85                  90                  95

Pro Pro Gly Leu Phe Gln Ala Ser Ala Thr Leu Asp Thr Leu Val Leu
            100                 105                 110

Lys Glu Asn Gln Leu Glu Val Leu Glu Val Ser Trp Leu His Gly Leu
        115                 120                 125

Lys Ala Leu Gly His Leu Asp Leu Ser Gly Asn Arg Leu Arg Lys Leu
    130                 135                 140

Pro Pro Gly Leu Leu Ala Asn Phe Thr Leu Leu Arg Thr Leu Asp Leu
145                 150                 155                 160

Gly Glu Asn Gln Leu Glu Thr Leu Pro Pro Asp Leu Leu Arg Gly Pro
                165                 170                 175

Leu Gln Leu Glu Arg Leu His Leu Glu Gly Asn Lys Leu Gln Val Leu
            180                 185                 190

Gly Lys Asp Leu Leu Leu Pro Gln Pro Asp Leu Arg Tyr Leu Phe Leu
        195                 200                 205

Asn Gly Asn Lys Leu Ala Arg Val Ala Ala Gly Ala Phe Gln Gly Leu
    210                 215                 220

Arg Gln Leu Asp Met Leu Asp Leu Ser Asn Asn Ser Leu Ala Ser Val
225                 230                 235                 240

Pro Glu Gly Leu Trp Ala Ser Leu Gly Gln Pro Asn Trp Asp Met Arg
                245                 250                 255
```

```
Asp Gly Phe Asp Ile Ser Gly Asn Pro Trp Ile Cys Asp Gln Asn Leu
            260                 265                 270

Ser Asp Leu Tyr Arg Trp Leu Gln Ala Gln Lys Asp Lys Met Phe Ser
        275                 280                 285

Gln Asn Asp Thr Arg Cys Ala Gly Pro Glu Ala Val Lys Gly Gln Thr
    290                 295                 300

Leu Leu Ala Val Ala Lys Ser Gln
305                 310

<210> SEQ ID NO 2
<211> LENGTH: 427
<212> TYPE: PRT
<213> ORGANISM: Homo sapiens

<400> SEQUENCE: 2

Asp Gln Thr Val Ser Asp Asn Glu Leu Gln Glu Met Ser Asn Gln Gly
1               5                   10                  15

Ser Lys Tyr Val Asn Lys Glu Ile Gln Asn Ala Val Asn Gly Val Lys
            20                  25                  30

Gln Ile Lys Thr Leu Ile Glu Lys Thr Asn Glu Glu Arg Lys Thr Leu
        35                  40                  45

Leu Ser Asn Leu Glu Glu Ala Lys Lys Lys Lys Glu Asp Ala Leu Asn
    50                  55                  60

Glu Thr Arg Glu Ser Glu Thr Lys Leu Lys Glu Leu Pro Gly Val Cys
65                  70                  75                  80

Asn Glu Thr Met Met Ala Leu Trp Glu Glu Cys Lys Pro Cys Leu Lys
                85                  90                  95

Gln Thr Cys Met Lys Phe Tyr Ala Arg Val Cys Arg Ser Gly Ser Gly
            100                 105                 110

Leu Val Gly Arg Gln Leu Glu Glu Phe Leu Asn Gln Ser Ser Pro Phe
        115                 120                 125

Tyr Phe Trp Met Asn Gly Asp Arg Ile Asp Ser Leu Leu Glu Asn Asp
    130                 135                 140

Arg Gln Gln Thr His Met Leu Asp Val Met Gln Asp His Phe Ser Arg
145                 150                 155                 160

Ala Ser Ser Ile Ile Asp Glu Leu Phe Gln Asp Arg Phe Phe Thr Arg
                165                 170                 175

Glu Pro Gln Asp Thr Tyr His Tyr Leu Pro Phe Ser Leu Pro His Arg
            180                 185                 190

Arg Pro His Phe Phe Pro Lys Ser Arg Ile Val Arg Ser Leu Met Pro
        195                 200                 205

Pro Phe Ser Pro Tyr Glu Pro Leu Asn Phe His Ala Met Phe Gln Pro
    210                 215                 220

Phe Leu Glu Met Ile His Glu Ala Gln Gln Ala Met Asp Ile His Phe
225                 230                 235                 240

His Ser Pro Ala Phe Gln His Pro Pro Thr Glu Phe Ile Arg Glu Gly
                245                 250                 255

Asp Asp Asp Arg Thr Val Cys Arg Glu Ile Arg His Asn Ser Thr Gly
            260                 265                 270

Cys Leu Arg Met Lys Asp Gln Cys Asp Lys Cys Arg Glu Ile Leu Ser
        275                 280                 285

Val Asp Cys Ser Thr Asn Asn Pro Ser Gln Ala Lys Leu Arg Arg Glu
    290                 295                 300

Leu Asp Glu Ser Leu Gln Val Ala Glu Arg Leu Thr Arg Lys Tyr Asn
305                 310                 315                 320
```

-continued

Glu Leu Leu Lys Ser Tyr Gln Trp Lys Met Leu Asn Thr Ser Ser Leu
                325                 330                 335

Leu Glu Gln Leu Asn Glu Gln Phe Asn Trp Val Ser Arg Leu Ala Asn
            340                 345                 350

Leu Thr Gln Gly Glu Asp Gln Tyr Tyr Leu Arg Val Thr Thr Val Ala
            355                 360                 365

Ser His Thr Ser Asp Ser Asp Val Pro Ser Gly Val Thr Glu Val Val
        370                 375                 380

Val Lys Leu Phe Asp Ser Asp Pro Ile Thr Val Thr Val Pro Val Glu
385                 390                 395                 400

Val Ser Arg Lys Asn Pro Lys Phe Met Glu Thr Val Ala Glu Lys Ala
                405                 410                 415

Leu Gln Glu Tyr Arg Lys Lys His Arg Glu Glu
                420                 425

<210> SEQ ID NO 3
<211> LENGTH: 394
<212> TYPE: PRT
<213> ORGANISM: Homo sapiens

<400> SEQUENCE: 3

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65              70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile

-continued

```
                260                 265                 270
Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                    325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 4
<211> LENGTH: 376
<212> TYPE: PRT
<213> ORGANISM: Homo sapiens

<400> SEQUENCE: 4

Glu Val Ser Ala Asp Gln Val Ala Thr Val Met Trp Asp Tyr Phe Ser
1               5                   10                  15

Gln Leu Ser Asn Asn Ala Lys Glu Ala Val Glu His Leu Gln Lys Ser
            20                  25                  30

Glu Leu Thr Gln Gln Leu Asn Ala Leu Phe Gln Asp Lys Leu Gly Glu
        35                  40                  45

Val Asn Thr Tyr Ala Gly Asp Leu Gln Lys Lys Leu Val Pro Phe Ala
    50                  55                  60

Thr Glu Leu His Glu Arg Leu Ala Lys Asp Ser Glu Lys Leu Lys Glu
65                  70                  75                  80

Glu Ile Gly Lys Glu Leu Glu Glu Leu Arg Ala Arg Leu Leu Pro His
                85                  90                  95

Ala Asn Glu Val Ser Gln Lys Ile Gly Asp Asn Leu Arg Glu Leu Gln
            100                 105                 110

Gln Arg Leu Glu Pro Tyr Ala Asp Gln Leu Arg Thr Gln Val Asn Thr
        115                 120                 125

Gln Ala Glu Gln Leu Arg Arg Gln Leu Thr Pro Tyr Ala Gln Arg Met
    130                 135                 140

Glu Arg Val Leu Arg Glu Asn Ala Asp Ser Leu Gln Ala Ser Leu Arg
145                 150                 155                 160

Pro His Ala Asp Glu Leu Lys Ala Lys Ile Asp Gln Asn Val Glu Glu
                165                 170                 175

Leu Lys Gly Arg Leu Thr Pro Tyr Ala Asp Glu Phe Lys Val Lys Ile
            180                 185                 190

Asp Gln Thr Val Glu Glu Leu Arg Arg Ser Leu Ala Pro Tyr Ala Gln
        195                 200                 205

Asp Thr Gln Glu Lys Leu Asn His Gln Leu Glu Gly Leu Thr Phe Gln
    210                 215                 220

Met Lys Lys Asn Ala Glu Glu Leu Lys Ala Arg Ile Ser Ala Ser Ala
225                 230                 235                 240
```

```
Glu Glu Leu Arg Gln Arg Leu Ala Pro Leu Ala Glu Asp Val Arg Gly
                245                 250                 255

Asn Leu Lys Gly Asn Thr Glu Gly Leu Gln Lys Ser Leu Ala Glu Leu
            260                 265                 270

Gly Gly His Leu Asp Gln Gln Val Glu Glu Phe Arg Arg Val Glu
        275                 280                 285

Pro Tyr Gly Glu Asn Phe Asn Lys Ala Leu Val Gln Gln Met Glu Gln
        290                 295                 300

Leu Arg Gln Lys Leu Gly Pro His Ala Gly Asp Val Glu Gly His Leu
305                 310                 315                 320

Ser Phe Leu Glu Lys Asp Leu Arg Asp Lys Val Asn Ser Phe Phe Ser
                325                 330                 335

Thr Phe Lys Glu Lys Glu Ser Gln Asp Lys Thr Leu Ser Leu Pro Glu
                340                 345                 350

Leu Glu Gln Gln Gln Glu Gln Gln Glu Gln Gln Glu Gln Val
            355                 360                 365

Gln Met Leu Ala Pro Leu Glu Ser
370                 375

<210> SEQ ID NO 5
<211> LENGTH: 127
<212> TYPE: PRT
<213> ORGANISM: Homo sapiens

<400> SEQUENCE: 5

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 6
<211> LENGTH: 249
<212> TYPE: PRT
<213> ORGANISM: Homo sapiens

<400> SEQUENCE: 6

Arg His Phe Trp Gln Gln Asp Glu Pro Pro Gln Ser Pro Trp Asp Arg
1               5                   10                  15

Val Lys Asp Leu Ala Thr Val Tyr Val Asp Val Leu Lys Asp Ser Gly
            20                  25                  30

Arg Asp Tyr Val Ser Gln Phe Glu Gly Ser Ala Leu Gly Lys Gln Leu
        35                  40                  45

Asn Leu Lys Leu Leu Asp Asn Trp Asp Ser Val Thr Ser Thr Phe Ser
    50                  55                  60
```

```
Lys Leu Arg Glu Gln Leu Gly Pro Val Thr Gln Glu Phe Trp Asp Asn
 65                  70                  75                  80

Leu Glu Lys Glu Thr Glu Gly Leu Arg Gln Glu Met Ser Lys Asp Leu
                 85                  90                  95

Glu Glu Val Lys Ala Lys Val Gln Pro Tyr Leu Asp Asp Phe Gln Lys
            100                 105                 110

Lys Trp Gln Glu Glu Met Glu Leu Tyr Arg Gln Lys Val Glu Pro Leu
        115                 120                 125

Arg Ala Glu Leu Gln Glu Gly Ala Arg Gln Lys Leu His Glu Leu Gln
    130                 135                 140

Glu Lys Leu Ser Pro Leu Gly Glu Glu Met Arg Asp Arg Ala Arg Ala
145                 150                 155                 160

His Val Asp Ala Leu Arg Thr His Leu Ala Pro Tyr Ser Asp Glu Leu
                165                 170                 175

Arg Gln Arg Leu Ala Ala Arg Leu Glu Ala Leu Lys Glu Asn Gly Gly
            180                 185                 190

Ala Arg Leu Ala Glu Tyr His Ala Lys Ala Thr Glu His Leu Ser Thr
        195                 200                 205

Leu Ser Glu Lys Ala Lys Pro Ala Leu Glu Asp Leu Arg Gln Gly Leu
    210                 215                 220

Leu Pro Val Leu Glu Ser Phe Lys Val Ser Phe Leu Ser Ala Leu Glu
225                 230                 235                 240

Glu Tyr Thr Lys Lys Leu Asn Thr Gln
                245

<210> SEQ ID NO 7
<211> LENGTH: 245
<212> TYPE: PRT
<213> ORGANISM: Homo sapiens

<400> SEQUENCE: 7

Ile Leu Gly Gly His Leu Asp Ala Lys Gly Ser Phe Pro Trp Gln Ala
  1               5                  10                  15

Lys Met Val Ser His His Asn Leu Thr Thr Gly Ala Thr Leu Ile Asn
                 20                  25                  30

Glu Gln Trp Leu Leu Thr Thr Ala Lys Asn Leu Phe Leu Asn His Ser
             35                  40                  45

Glu Asn Ala Thr Ala Lys Asp Ile Ala Pro Thr Leu Thr Leu Tyr Val
 50                  55                  60

Gly Lys Lys Gln Leu Val Glu Ile Glu Lys Val Val Leu His Pro Asn
 65                  70                  75                  80

Tyr Ser Gln Val Asp Ile Gly Leu Ile Lys Leu Lys Gln Lys Val Ser
                 85                  90                  95

Val Asn Glu Arg Val Met Pro Ile Cys Leu Pro Ser Lys Asp Tyr Ala
            100                 105                 110

Glu Val Gly Arg Val Gly Tyr Val Ser Gly Trp Gly Arg Asn Ala Asn
        115                 120                 125

Phe Lys Phe Thr Asp His Leu Lys Tyr Val Met Leu Pro Val Ala Asp
    130                 135                 140

Gln Asp Gln Cys Ile Arg His Tyr Glu Gly Ser Thr Val Pro Glu Lys
145                 150                 155                 160

Lys Thr Pro Lys Ser Pro Val Gly Val Gln Pro Ile Leu Asn Glu His
                165                 170                 175

Thr Phe Cys Ala Gly Met Ser Lys Tyr Gln Glu Asp Thr Cys Tyr Gly
            180                 185                 190
```

```
Asp Ala Gly Ser Ala Phe Ala Val His Asp Leu Glu Glu Asp Thr Trp
        195                 200                 205

Tyr Ala Thr Gly Ile Leu Ser Phe Asp Lys Ser Cys Ala Val Ala Glu
        210                 215                 220

Tyr Gly Val Tyr Val Lys Val Thr Ser Ile Gln Asp Trp Val Gln Lys
225                 230                 235                 240

Thr Ile Ala Glu Asn
            245

<210> SEQ ID NO 8
<211> LENGTH: 142
<212> TYPE: PRT
<213> ORGANISM: Homo sapiens

<400> SEQUENCE: 8

Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln
    130                 135                 140

<210> SEQ ID NO 9
<211> LENGTH: 326
<212> TYPE: PRT
<213> ORGANISM: Homo sapiens

<400> SEQUENCE: 9

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110

Pro Glu Leu Pro Val Cys Ala Pro Ile Ile Cys Pro Pro Pro Ser Ile
        115                 120                 125
```

```
-continued

Pro Thr Phe Ala Thr Leu Arg Val Tyr Lys Pro Ser Ala Gly Asn Asn
    130              135              140

Ser Leu Tyr Arg Asp Thr Ala Val Phe Glu Cys Leu Pro Gln His Ala
145              150              155              160

Met Phe Gly Asn Asp Thr Ile Thr Cys Thr Thr His Gly Asn Trp Thr
            165              170              175

Lys Leu Pro Glu Cys Arg Glu Val Lys Cys Pro Phe Pro Ser Arg Pro
            180              185              190

Asp Asn Gly Phe Val Asn Tyr Pro Ala Lys Pro Thr Leu Tyr Tyr Lys
        195              200              205

Asp Lys Ala Thr Phe Gly Cys His Asp Gly Tyr Ser Leu Asp Gly Pro
    210              215              220

Glu Glu Ile Glu Cys Thr Lys Leu Gly Asn Trp Ser Ala Met Pro Ser
225              230              235              240

Cys Lys Ala Ser Cys Lys Val Pro Val Lys Lys Ala Thr Val Val Tyr
            245              250              255

Gln Gly Glu Arg Val Lys Ile Gln Glu Lys Phe Lys Asn Gly Met Leu
            260              265              270

His Gly Asp Lys Val Ser Phe Phe Cys Lys Asn Lys Glu Lys Lys Cys
            275              280              285

Ser Tyr Thr Glu Asp Ala Gln Cys Ile Asp Gly Thr Ile Glu Val Pro
    290              295              300

Lys Cys Phe Lys Glu His Ser Ser Leu Ala Phe Trp Lys Thr Asp Ala
305              310              315              320

Ser Asp Val Lys Pro Cys
                325
```

PROTEIN MARKERS FOR DIAGNOSING STOMACH CANCER AND THE DIAGNOSTIC KIT USING THEM

CROSS REFERENCE TO RELATED APPLICATIONS

This is the U.S. National Stage of International Application No. PCT/KR2006/005836, filed Dec. 28, 2006, which was published in English under PCT Article 21(2), which in turn claims the benefit of Korean Application No. 10-2006-0019517, filed Feb. 28, 2006. Both applications are incorporated herein in their entirety.

TECHNICAL FIELD

The present invention relates to protein markers for diagnosing stomach cancer and the diagnostic kit using the same, more precisely protein markers for diagnosing stomach cancer screened by two-dimensional gel electrophoresis and bioinformatics and the diagnostic kit using the same.

BACKGROUND ART

Cancer is now a leading cause of death by overtaking heart disease in the $21^{st}$ century. So, the prevention, diagnosis and treatment of cancer are major concerns in the whole world. Korea is not an exception. Since 1988, cancer has been the leading cause of death in Korea. In the case of stomach cancer, it has been reduced in America and European countries but it still exhibits the highest outbreak frequency in Korea and Japan. According to the report of Cancer Registry, Seoul, Korea (1992-95), stomach cancer patients take 23% of total cancer patients (male: 24.7%, female: 17.3%). The average age of outbreak is 54, mostly 40-60 but the age of 20 s takes approximately 3% and the frequency of the disease in men is double that in women. However, once it is early diagnosed, survival rate is at least 90%, suggesting that early diagnosis of stomach cancer is very important for the National Health Care Surveillance.

Tumorigenesis, progress and malignant change are the result of combined action of both genetic factors and environmental factors to result in proteome changes. The correlation between the level of molecular concentrations of proteins, directly involved in essential metabolism and regulation pathways for the survival of every cells including cancer cells, and the relevant mRNA level is very low (correlation coefficient=0.48), so the mRNA focused approach based on high-throughput screening of a target gene might lead to misunderstanding on the biological functions of the target protein. The activity, stability, intracellular location and turnover of the protein involved in cell survival, differentiation and death are regulated by diverse post-translational modifications (PTM). Thus, it is more important to analyze proteome than to focus on mRNA.

Cancer is a systemic disease, in which rather many functions and biological processes of various organs than one or two kinds of cells or tissues are involved. Therefore, such clinical samples, which are able to reflect the whole proteome changes, such as, in serum or body fluid, have to be examined. In fact, general clinical diagnosis has been made through the analysis of the body fluid. So, developing a novel diagnostic method using body fluid that facilitates the effective primary screening might pave the way to significant improvement of survival rate of cancer patients.

The combination of biotechnology (BT) and information technology (IT) gave birth to bioinformatics and bioelectronics that facilitate easy, fast and effective analysis of huge amount of data. Particularly, bioinformatics is a technique to collect, store and analyze huge amount of information that a living body contains, and to use such information in the field of drug development, food production, agriculture and environmental business, etc, resulting in the establishment of biological information S/W, biological information service, and information technology infrastructure. The image mining is a new database applying technique, which is technical combination of image database technique and data mining technique. Unlike the general data mining tried in the field of bioinformatics, the image mining is a novel technique never tried before in domestic and overseas. General data mining techniques are based on applied statistics, suggesting that it is limited in obtaining precise relevant information. For example, proteome spots, seen on the image made by two-dimensional gel electrophoresis, are expected to include information on the disease condition (normal or ill) and various characteristics of the patient. So, if it is possible to extract relevant information by using the image mining technique, diagnostic method and prediction of prognosis, depending on stage and histopathological classification, will be significantly improved and/or complemented.

Korean Patent No. 2004-0055893 describes the automatic template generation method for constructing protein interaction networks, and Korean Patent No. 2003-0092462 describes the method and kit for diagnosis of progress stage of cancer by investigating the level of p53 protein or Bcl-X L protein or the correlation of the two and Bcl-2 protein. However, these two descriptions do not include the explanations on the stomach cancer marker development by using two-dimensional gel electrophoresis and bioinformatics.

DISCLOSURE

Technical Problem

It is an object of the present invention to provide a method for screening a marker protein for diagnosing stomach cancer, which characteristically differs in expression in stomach cancer, by using two-dimensional gel electrophoresis and bioinformatics and a use of the marker as an early diagnosis marker for stomach cancer.

Technical Solution

To achieve the above object, the present invention provides a screening method of stomach cancer high risk group comprising the following steps: (1) investigating the presence or absence of one or more markers for diagnosing stomach cancer in the sample obtained from a patient, selected from a group consisting of Leucine-rich alpha-2-glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H, and the expression levels or patterns of them; and (2) analyzing the relation of the screening result and stomach cancer progression status.

The present invention also provides a use of the protein selected from a group consisting of Leucine-rich alpha-2-glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H as a marker for diagnosing stomach cancer.

The present invention further provides a diagnostic kit for stomach cancer containing (1) primary capture reagent binding to one or more markers for diagnosing stomach cancer selected from a group consisting of Leucine-rich alpha-2- glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H; and (2) secondary capture reagent which was not bound to the first capture reagent.

The descriptions on terms used in the present invention are given below to help the understanding of the present invention.

"Marker" indicates the substance, which is distinctly found in the serum sample of a certain disease patient, but not in normal serum samples. The marker or markers comprise a single polypeptide or a combination of polypeptides.

"Proteome pattern" indicates a specific polypeptide group or grouping of polypeptides distinctly found in the serum sample obtained from a patient with a certain disease but not in normal serum samples. For example, a serum protein group, exhibiting specific changes in its level by a disease, and/or two-dimensional location and morphology of the group is included in this criterion.

"Data mining" indicates the procedure designed to find out correlation between relevant data, more precisely, the procedure in which a new data model is extracted from the stored data of database, which has not been disclosed yet, and useful information in the future is taken from the new data model and applied to decision-making. That is, relevant information is extracted by investigating patterns hidden in the data.

Hereinafter, the present invention is described in detail.

The present invention provides a screening method of stomach cancer high risk group comprising the following steps: (1) investigating the presence or absence of one or more markers for diagnosing stomach cancer in the sample obtained from a patient, selected from a group consisting of Leucine-rich alpha-2-glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H, and the expression levels or patterns of them; and (2) analyzing the relation of the screening result and the state of stomach cancer progress.

In step (2), the state of stomach cancer indicates the stomach cancer risk level of an individual, whether stomach cancer has developed or the degree of stomach cancer progression.

The present inventors obtained serum samples from normal healthy individuals and cancer patients, followed by the two-dimensional image treatment for the serum proteome. Then, bioinformatics was applied to analyze the prepared data and as a result the optimum marker proteins being able to distinguish a normal individual from a cancer patient were identified.

Particularly, the present inventors performed two-dimensional gel electrophoresis to establish image data of proteins exhibiting significant expression level changes according to cancer development (herein, stomach cancer), to which bioinformatics techniques were applied, resulting in the establishment of a novel use of the protein markers for diagnosing stomach cancer. First of all, sera were collected from both healthy people and cancer patients. The stomach cancer patients were at average 58.7 year-old male (age between 33-78) and at average 56.2 year-old female (age between 29-77) (see Table 1).

Optimum conditions for two-dimensional gel electrophoresis to examine serum proteomes were investigated. As a result, to give the best results, 13 cm strip was used, pH range was 4-7, total volt hour for IEF (isoelectric focusing) was 62,000 Vhr, amount of serum protein loaded was 200 ug, and composition of the rehydration buffer was 8 M urea.

Upon completion of electrophoresis, proteins were detected by the staining patterns. To detect spots on the images of two-dimensional electrophoresis gel, a computer software was used to establish bases for image comparison. Particularly, spots were detected by image filtering, subtracting background, removing vertical and horizontal streaks, and comparing variants using a computer software program. And the database was established with the results.

When samples were measured and thereby database was established, the data was analyzed by bioinformatics approach. The software used in bioinformatics can constitute codes to change the image data into readable codes, which includes the code for applying algorithm to the information on the markers provided by the present invention. In a preferred embodiment of the present invention, various bioinformatics techniques were used to screen a stomach cancer associated protein marker. The analysis used in the present invention using bioinformatics techniques comprises the steps of generating an example of the proteome harboring disease-specific proteome pattern and training to establish database (training stage); and extracting specific data of target serum proteome and comparing it with the above disease-specific proteome example to determine the disease outbreak in the target serum proteome (testing stage).

"Training" herein indicates that the generation of a classification model by algorithm using established data of known samples from stomach cancer patients and normal healthy people. At this time, the data used to generate a classification model is named "training data set" and the groups providing the data is named "training group". Once training is finished, the classification model recognizes a data pattern from unknown samples and classifies it.

Support vector machine is a learning program facilitating pattern recognition, which is able to treat multiple variants at the same time and classify them. This support vector machine can interpret nonlinear data of the input area into linear data and provide optimal boundary (optimal separating plane or hyperplane) between each characteristics. The support vector machine is divided largely into training process and evaluating process. In the training process, support vector is generated. And in the evaluating process, judgment is made considering specified characteristics. Sample is composed of n objects, and the $i^{th}$ object is represented as vector xi comprising p variants and then the corresponding class which has been pre-classified is indicated as yi. So, if there are two classes, yi is either '1' or '−1' (cancer or normal). Discriminant function for the random input pattern is as follow.

$$D(x) = \text{sign}(wx+b) = \begin{cases} +1, & \text{if } wx+b \geq 0 \\ -1, & \text{else} \end{cases}$$

w: weight vector
b: threshold

The optimal hyperplane dividing the data into two classes is the dotted line in the following graph. The two dotted lines and margin (d) are as follows.

$$(w \cdot x)+b=\pm 1, d=2/\|w\|$$

To design a support vector adequate for the purpose, weight vector (w) and boundary (b) have to be determined. That is, according to the formula: $y[(w \cdot x)+b] \geq 1$, w and b which are able to minimize $\|w\|$ are screened.

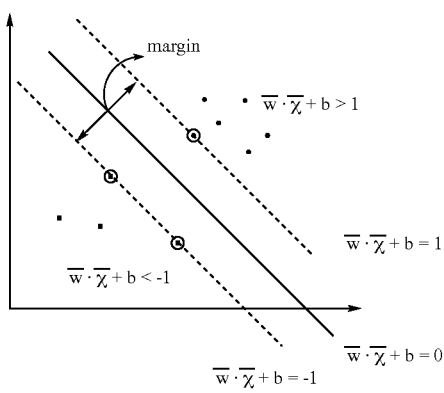

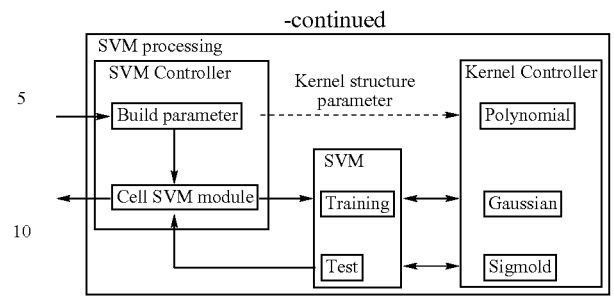

Genetic algorithm is making an engineering model from genetic and evolutionary systems of natural world, which is dealing with adaptation capacity of a life to environment. The possible solutions for a question are expressed in a certain form and then gradually modified to produce more valuable solutions. Particularly, genetic algorithm is a kind of optimizing algorithm for searching x value calculating the maximum value or the minimum value of the function f(x) against variant x defined in a specific area, as fast as possible. Genetic algorithm is composed of the following steps: determining genotype which encodes and converts genetic factors into symbol string; determining early genetic group to generate various individuals having different characteristics from the defined genotype above; evaluating adaptation of each individual to calculate the adaptation according to the pre-defined method; selecting individuals based on the evaluated adaptation in order to determine survival distribution of individuals; mating by substituting a gene between two chromosomes to generate a new individual; mutating by modifying a part of a gene and maximizing diversity of the genetic group so as to prepare individuals providing better solutions; and returning to the step of evaluating adaptation of each individual. Genetic algorithm facilitates searching for solutions according to cooperative genetic manipulation on selection, mating, etc, among multiple individuals. Thus, compared with the conventional parallel screening method for solutions, genetic algorithm is easy and simple to screen solutions.

The process of interlocking of GA with SVM is as follows.

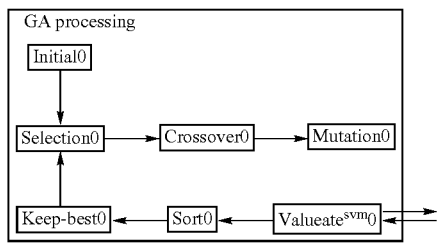

Among proteome data obtained from 311 volunteers (stomach cancer patients; 143, normal healthy people; 168), 100 of each stomach cancer patients and normal people were randomly selected and form a training group and evaluating group (see Table 2). The training group data of 200 people was applied to genetic algorithm (GA) interlocked to support vector machine (SVM) (see Korean Patent No. 10-2002-0067298 "Method and System for Analysis of Cancer Biomarkers Using Proteome Image Mining") and as a result 9 markers for diagnosing stomach cancer were found and database was constructed. Mean values of cancer patients and normal people were calculated with each spot on database, which were then compared. T-test was performed to calculate p-value of each group and 9 spots exhibiting significant difference in expression were identified (see Table 3).

Cross validation and random forest, other bioinformatics techniques, were performed with the proteins of the training group. As a result, stomach cancer decision rate (sensitivity—diagnose a cancer patient as cancer; specificity—diagnose a normal person as normal) was high according to the method of the invention. Random forest was performed again with the data of 111 remaining people who were not included in the training group (stomach cancer patients: 43, normal healthy people: 68), and as a result two algorithm exhibited up to 80% diagnostic accuracy. Therefore, 9 marker candidate proteins for diagnosing stomach cancer were confirmed to be very useful. To support the result, immunoblotting was performed and the result was consistent, that is, marker protein candidates exhibited significant difference in expression level between normal sera and stomach cancer patient sera.

The data of total 143 stomach cancer patients (training group: 100, evaluating group: 43) are divided by cancer stage and the expressions of those 9 proteins were investigated according to the stage. As shown in FIG. 3, each protein exhibited different expressions according to the stage. The expressions of Leucine-rich alpha-2-glycoprotein (LRG), Clusterin, Alpha-1-antitrypsin, ProApolipoprotein A-I, Haptoglobin beta, Haptoglobin alpha-2 and Apolipoprotein H were higher in stomach cancer patients than in normal healthy group, whereas the expressions of Apolipoprotein A-IV and Transthyretin were reduced in stomach cancer patients. Thus, those 9 marker proteins are presumably associated with stomach cancer progress, supporting the usability of those proteins as biomarkers for diagnosing stomach cancer.

Markers of the present invention facilitate the screening methods, precisely proteomes of target sera to be investigated to detect stomach cancer were inputted and changed into two-dimensional image, which was then compared with the sample having the pattern of disease-specific marker protein. Or the expressions of those marker proteins in target sera were compared with those in normal sera, and those expressions were turned into numerical values. From the comparison of those values, it could be judged whether the target serum is normal or with cancer.

The present invention also provides a use of the protein selected from a group consisting of Leucine-rich alpha-2-glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H as a marker for diagnosing stomach cancer.

The above 9 proteins can be used as markers for diagnosing stomach cancer since they were confirmed to be associated with stomach cancer progress.

The present invention further provides a diagnostic kit for stomach cancer containing primary capture reagent binding to one or more markers for diagnosing stomach cancer selected from a group consisting of Leucine-rich alpha-2-glycoprotein (LRG), Clusterin, Alpha-1-antitrypsin, Apolipoprotein A-IV, Transthyretin, ProApolipoprotein A-I, Haptoglobin beta, Haptoglobin alpha-2 and Apolipoprotein H; and secondary capture reagent which was not bound to the first capture reagent.

The diagnostic kit can be used to detect one or more markers of the invention that exhibit different expressions in stomach cancer patients. The diagnostic kit of the present invention facilitates not only the diagnosis of cancer by a doctor but also the monitoring of the after-care response of a patient, in order to modify the treatment. The kit can also be used to identify a compound regulating in vivo or ex vivo expression of one or more markers in stomach cancer models (for example: animal models such as mice, rats, etc).

The primary capture reagent is an antibody or a metal chelate, more preferably an antibody. The secondary capture reagent is a conjugate labeled with a coloring enzyme, a fluorescein, a radio-isotope or a colloid, which acts as a secondary antibody. The coloring enzyme can be peroxidase, alkaline phosphatase or acid phosphatase (ex: horseradish peroxidase). The fluorescein can be fluorescein carboxylic acid (FCA), fluorescein isothiocyanate (FITC), fluorescein thiourea (FTH), 7-acetoxycoumarin-3-yl, fluorescein-5-yl, fluorescein-6-yl, 2',7'-dichlorofluorescein-5-yl, 2',7'-dichlorofluorescein-6-yl, dihydrotetramethylrosamine-4-yl, tetramethylrodamine-5-yl, tetramethylrodamine-6-yl, 4,4-difluoro-5,7-dimethyl-4-bora-3a,4a-diaza-s-indacene-3-ethyl or 4,4-difluoro-5,7-diphenyl-4-bora-3a,4a-diaza-s-indacene-3-ethyl.

When a sample of a patient is exposed on the primary capture reagent, preferably a marker-specific antibody, the sample can be diluted before exposure on the antibody and the antibody can be fixed in a solid phase in order to be used in the next phases including washing or complex separation, etc. The solid phase can be glass or plastic such as microtiter plate, rod, bead or microbead, etc. The antibody can be bound to probe substrate or protein chip. After incubating the sample with the antibody, the sample was washed and incubated with the secondary capture reagent, preferably secondary antibody to measure antibody-marker complex. The measurement or detection of the antibody-marker complex can be performed by one of the processes of fluorescence, luminescence, chemiluminescence, optical density, reflection and transmission. In addition to those methods above, markers in the sample can be detected by indirect methods such as competition or inhibition test with a monoclonal antibody binding to another epitope of the marker.

The kit excludes a substrate to react with an enzyme and a non-bound protein, but includes washed solution or eluent containing bound biomarkers only. Samples for the analysis include serum, urine, tear, saliva and other biomaterials containing disease-specific polypeptide. Preferably, the samples are biological liquid samples such as blood, serum, and plasma, and more preferably serum. Samples can be prepared in order to increase the sensitivity of marker detection. For example, sera obtained from patients can be pre-treated by anion exchange chromatography, affinity chromatography, size exclusion chromatography, liquid chromatography, sequential extraction or gel electrophoresis.

DESCRIPTION OF DRAWINGS

The application of the preferred embodiments of the present invention is best understood with reference to the accompanying drawings, wherein:

FIG. 1 is a set of photographs illustrating the whole image of the representative serum proteome seen on two-dimensional gel electrophoresis and the optimal urea concentration for the two-dimensional gel electrophoresis.

1: whole image of two-dimensional gel electrophoresis

2: 8 M urea

3: 2 M thiourea/7 urea

FIG. 2 is a set of photographs illustrating the proteins exhibiting different expressions in cancer patients, compared with in normal healthy people, detected by two-dimensional gel electrophoresis.

FIG. 3 is a set of graphs illustrating the stomach cancer stage dependent protein expression.

A: Haptoglobin beta

B: Haptoglobin alpha

C: Leucine-rich alpha-2-glycoprotein (LRG)

D: A1 antitrypsin

E: ProApolipoprotein A-I

F: Apolipoprotein H

G: Clusterin

H: Apolipoprotein A-IV

I: Transthyretin

FIG. 4 is a set of photographs illustrating the expression levels of marker proteins in stomach cancer patients which are different from those in normal healthy people, detected by immunoblotting.

NS: normal serum

SC: stomach cancer serum

| Haptoglobin beta | |
|---|---|
| 1. Marker | |
| 2. NS | 0.08 μl |
| 3. SC | 0.08 μl |

| Haptoglobin alpha | |
|---|---|
| 1. his-Hp α2 | 50 ng |
| 2. NS | 0.04 μl |
| 3. SC | 0.04 μl |
| 4. NS | 0.08 μl |
| 5. SC | 0.08 μl |
| 6. Haptoglobin | 50 ng |
| 7. Marker | |

| Transthyretin | |
|---|---|
| 1. Marker | |
| 2. NS | 0.0016 μl |
| 3. SC | 0.0016 μl |
| 4. NS | 0.0032 μl |
| 5. SC | 0.0032 μl |
| 6. NS | 0.0064 μl |
| 7. SC | 0.0064 μl |
| 8. NS | 0.0128 μl |
| 9. SC | 0.0128 μl |

| Alpha-1-antitrypsin | |
|---|---|
| 1. Marker | |
| 2. NS | 0.0064 μl |
| 3. SC | 0.0064 μl |
| 4. NS | 0.0096 μl |
| 5. SC | 0.0096 μl |
| 6. a1 antitrypsin | 48 ng |

Mode for Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Two-Dimensional Gel Electrophoresis

<1-1> Serum Obtainment

Peripheral blood was obtained from stomach cancer patients (143 people) at Department of Surgery, Seoul National University College of Medicine, for two and a half years before the patients got surgery and normal peripheral blood was also obtained from normal healthy people (168 people) proved not to have stomach cancer by medical examination at the Green Cross Reference Lab. Blood was taken by using vacutainer SST II tube (Becton Dickinson) and sera were separated by centrifugation.

TABLE 1

| Serum obtein | | | | | | | | | |
|---|---|---|---|---|---|---|---|---|---|
| sex | | | age | | | | | | |
| male | female | | 20 | 30 | 40 | 50 | 60 | 70 | |
| 186 | 125 | cancer | 1 | 11 | 21 | 40 | 45 | 25 | 143 |
| | | normal | 0 | 14 | 38 | 65 | 46 | 15 | 168 |
| | | stage | | | | | | | |
| | | | 1 | 2 | 3 | 4 | | | |
| | | cancer | 53 | 36 | 34 | 20 | | | 143 | total 311 people

<1-2> Optimization of Conditions for Two-Dimensional Gel Electrophoresis

<1-2-1> Establishment of Method for Two-Dimensional Gel Electrophoresis

Various experimental conditions were checked to exhibit serum proteome. First, immobilized pH gradient (IPG) strip (Amersham Bioscience) for IEF (isoelectric focusing) was 13 cm long and pH was set at the range between 4 and 7 considering experimental time and efficient detection of the serum proteome. During IEF, the total volt hour was 62,000 Vhr, which was proved to be optimal volt hour. The amount of each sample for loading was determined to be 200 ug and the whole image generated on two-dimensional gel electrophoresis is shown in FIG. 1-1.

<1-2-2> Establishment of a Method for Sample Treatment

To determine the optimal composition of rehydration buffer used for the analysis of serum proteome, the condition with 8 M urea (Sigma) (FIG. 1-2) and the condition with 7 M urea/2 M thiourea (Sigma) (FIG. 1-3) were compared. As a result, when thiourea was used, vertical streaks were often seen, which made spot analysis difficult. So, the optimal condition for the buffer was determined 8 M urea (FIG. 1-2).

<1-2-3> Establishment of a Method for Protein Staining

Silver stain is a staining method for detecting small amount of protein, which has been often used in laboratories. However, because of the difficulty in reproducibility and the covalent bond between glutaraldehyde of a reagent with a target protein, this method cannot be used for MALDI-TOF Mass Spectrometry. To overcome the above problems, the present inventors minimized deviations of staining process by keeping recommended volume of a solution and reaction time strictly. To construct image database, the present inventors stained the protein with SyproRuby (Molecular Probe) exhibiting excellent reproducibility and quantitative results.

<1-3> Two-Dimensional Gel Electrophoresis

200 μg of serum protein was loaded in 2% SDS (Sigma)/100 mM Dithiothreitol solution (DTT, Sigma), followed by heating at 95° C. for 5 minutes. The solution was loaded in rehydration solution (8 M Urea, 4% CHAPS (Sigma), 50 mM DTT, 0.5% IPG buffer (Amersham Bioscience)), followed by stirring. Centrifugation was performed at room temperature to separate supernatant. IEF (isoelectric focusing) was performed with IPGphor system (Amersham Biosciences) using Immobilized pH Gradient (IPG) strip (pH4-7, 13 cm Amersham Bioscience). SDS-PAGE was performed by vertical electrophoresis using 12.5% polyacrylamide gel. Upon completion of electrophoresis, proteins were stained with SyproRuby (Molecular Probe), followed by detection. Gel images of the two-dimensional gel electrophoresis were analyzed by PDQuest software (Bio-Rad).

EXAMPLE 2

Construction of Image Database

To determine optimal conditions, various factors were regulated such as image filtering, background eliminating, uneven vertical streak eliminating, uneven horizontal streak eliminating and spot variant detecting. Spots on image were detected and then specifically distinguishable 110 spots were precisely analyzed. Deviations generated during sample measurement or mechanical deviations generated during image obtainment were normalized by dividing the amount of each spot by the sum of all the spots, in order to regulate the darkness of two-dimensional gel electrophoresis image caused not by the difference of protein expression but by other factors.

EXAMPLE 3

Bioinformatics Analysis

To screen a marker protein in serum, which is associated with stomach cancer, bioinformatics analysis was performed.

As shown in Table 1, 100 people from each stomach cancer patient group and normal healthy people group were randomly selected out of the proteome data of total 311 people (stomach cancer patients 143, and normal healthy people 168) to form a training group. The training group data of the selected 200 people was interlocked with support vector machine (SVM) and genetic algorithm (GA) (see Korean Patent No. 10-2002-0067298 "Method and System for Analysis of Cancer Biomarkers Using Proteome Image Mining") to screen marker protein candidates for diagnosing stomach cancer (Table 3).

The data of the remaining 111 people not included in the training group (stomach cancer patient 43, and normal healthy people 68) was tested to confirm the usability of those marker protein candidates selected from the training as a diagnostic marker for stomach cancer. Each experimental stage is described in more detail hereinafter.

TABLE 2

| Distribution of sex, age and stage | | | | | | | | | | |
|---|---|---|---|---|---|---|---|---|---|---|
| (A) training group | | | | | | | | | | |
| sex | | | | age | | | | | | |
| male | female | | | 20 | 30 | 40 | 50 | 60 | 70 | |
| 121 | 79 | cancer | | 1 | 6 | 12 | 24 | 36 | 21 | 100 |
|  |  | normal | | 0 | 7 | 27 | 27 | 27 | 12 | 100 |
| stage | | | | | | | | | | |
|  |  |  | 1 | 2 | 3 | 4 | | | | |
| cancer | | | 42 | 23 | 23 | 12 | | | | 100 |
| (B) evaluating group | | | | | | | | | | |
| sex | | | | age | | | | | | |
| male | female | | | 20 | 30 | 40 | 50 | 60 | 70 | |
| 65 | 46 | cancer | | 0 | 5 | 9 | 16 | 9 | 4 | 43 |
|  |  | normal | | 0 | 7 | 11 | 28 | 19 | 3 | 68 |
| stage | | | | | | | | | | |
|  |  |  | 1 | 2 | 3 | 4 | | | | |
| cancer | | | 11 | 13 | 11 | 8 | | | | 43 | total 311 people
*Gender and age distributions of normal healthy people and stomach cancer patients volunteered for the above data analysis were presented according to the training group (A, 200 people) and the evaluating group (B, 111 people).

<3-1> Marker Protein Selection by SVM/GA

To screen marker proteins that facilitate the distinguishment of stomach cancer group from normal healthy group, proteome data of 100 stomach cancer patients and 100 normal healthy people were interlocked with support vector machine (V. N. Vapnik et. al., Theory of Support Vector Machines, Technical Report CSD-TR-96-17, Univ. of London, 1996.) and genetic algorithm followed by training. As a result, optimal spots (9) which would be markers for stomach cancer owing to their high training result (sensitivity: 91% and specificity: 97%) were screened.

<3-2> T-Test

T-test was performed to determine whether the difference of expression of the marker protein for diagnosing stomach cancer screened in the above Example between normal healthy people and stomach cancer patients was significant enough to determine the protein as a marker. Particularly, mean values of expressions were compared between stomach cancer patients and normal healthy-people by using SAS program (Statistical Analysis System Institute Inc.) and p-values were obtained. When $p<0.05$, it was judged that the difference was statistically significant. As shown in Table 3, t-test confirmed that 9 spots were screened with suggestion that they were the proteins exhibiting significant differences in expression levels between normal healthy people and stomach cancer patients.

TABLE 3

| Marker protein | LRG | Clusterin | Alpha-1-antitrypsin | Apolipoprotein A-IV | Transthyretin | Pro-Apolipoprotein A-I | Haptoglobin beta | Haptoglobin alpha-2 | Apolipoprotein H |
|---|---|---|---|---|---|---|---|---|---|
| t-test | 1.32E−07 | 4.24E−02 | 3.12E−05 | 3.82E−05 | 6.41E−07 | 3.85E−08 | 1.16E−07 | 3.85E−14 | 3.32E−04 |

<3-3> Diagnosis by Random Forest

The marker protein candidates for, diagnosing stomach cancer, screened by SVM/GA in the above Example, were applied to Random Forest (results of multiple tree-classification determinants were integrated according to majority rule, which would be the final classified result, L. Breiman, "Random forests", Machine Learning, Vol. 45. Issue 1, October 2001), another bioinformatics algorithm. The result was consistent with that obtained by SVM/GA analysis above, that is the equal training group of 200 people also exhibited high decision rate of 80.0% (sensitivity 78%, and specificity 82%).

<3-4> Cross-Validation

To investigate errors of the training group selected at random, cross-validation was performed by leave-one-out (a method to presume generalized errors, in which data were divided into same sized k subsets and k−1 groups were determined to be a training group and the remaining one is determined to be an evaluating group and this classification experiment was performed k times and the average error according to k times was calculated). As a result, decision rate was 81.5% (sensitivity 78%, and specificity 85%).

<3-5> Identification of the Selected Proteins

Each spot on two-dimensional electrophoresis gel was picked and put in a tube containing distilled water, followed by trypsin digestion in gel, resulting in peptides. The peptides were tested at Korea Basic Science Institute, Taejon, Korea. The proteins were analyzed by MALDI-TOF-TOF (ABI 4700 Proteomics Analyzer) and the spectrums were screened by peptide mass finger print and MS/MS ion search from the database to identify the proteins (Michael O. Glocker et al., Proteomics, 4: 3921-3032, 2004).

<3-6> Verification of the Selected Proteins

To confirm the competence of the selected marker protein candidates for diagnosing stomach cancer to distinguish cancer from normal, random forest was performed this time not with the training group proteome but with the evaluating group proteome (111 people who were not included in the training group; 43 stomach cancer patients, 68 normal healthy people). From the result of support vector machine algorithm was confirmed that the marker protein candidates had sensitivity of 81.39% and specificity of 77.94%. Random forest algorithm gave the result that the marker protein candidates had sensitivity of 86.05% and specificity of 82.35%. Two different algorithms consistently proved that the candidates had high sensitivity around 80%, suggesting that these candidates are very useful as marker proteins.

EXAMPLE 4

Verification of Marker Proteins for Diagnosing Stomach Cancer—Immunoblotting

To investigate expression levels of marker proteins for diagnosing stomach cancer in normal sera and in stomach cancer patient sera, pooled serum samples were prepared from 50 people of each group: normal healthy people and stomach cancer patients, followed by immunoblotting using an antibody against each protein. As a result, as shown in FIG. 4, the marker protein levels in sera of stomach cancer patients were increased or reduced, compared with those in normal sera (FIG. 4).

1) Alpha-1-Antitrypsin

Human serum was diluted with distilled water and 5× sample buffer (0.0016 ul serum/1 ul sample), which was loaded on 12% SDS-PAGE at different volumes of 1, 2, 4, and 6 ul. 48 ng of alpha-1-antitrypsin (Sigma) was loaded as a positive control, followed by electrophoresis with 25 mA. Western blotting was performed. Particularly, the gel was transferred onto PVDF membrane, followed by blocking with 5% skimmed milk/PBST (0.05% Tween 20). The membrane was treated with alpha-1-antitrypsin antibody (chicken IgY, Abcam) diluted (1:10000) in 5% skim milk/PBST (primary treatment) and anti-chicken IgY-HRP (1:20000, Abcam) (secondary treatment).

2) Haptoglobin Alpha

Human serum was diluted (0.04 ul serum/1 ul sample), which was loaded on SDS-PAGE. Purified His-Hp α2 and 50 ng of haptoglobin (Sigma) were loaded as a positive control. Polyclonal anti-Haptoglobin alpha (1:1000) was treated as a primary antibody and anti-Rabbit IgG-HRP (1:20000, Sigma) was treated as a secondary antibody. The polyclonal anti-Haptoglobin alpha used as a primary antibody was prepared by injecting recombinant his-haptoglobin alpha 2 into a rabbit, which was provided by Asan Medical Center, Seoul, Korea. (his-Hp: recombinant fusion protein labeled with haptoglobin histidine)

3) Haptoglobin Beta

Human serum was diluted (0.04 ul serum/1 ul sample), which was loaded on SDS-PAGE. Polyclonal anti-Haptoglobin (1:5000, Sigma) was treated as a primary antibody and anti-mouse IgG-HRP (1:20000, Sigma) was treated as a secondary antibody.

4) Transthyretin

Human serum was diluted (0.0016 ul serum/1 ul sample), which was loaded on SDS-PAGE. Polyclonal anti-transthyretin (1:1000, Dakocytomation, Inc.) was treated as a primary antibody and anti-rabbit IgG-HRP (1:20000, Sigma) was treated as a secondary antibody.

5) ProApolipoprotein A-I

ProApolipoprotein A-I is the precursor of Apolipoprotein A-I in which 7 amino acids at N-terminal were fallen apart. An antibody that is able to distinguish ProApolipoprotein A-1 from Apolipoprotein A-1 could not be obtained or constructed, and thus it was impossible to detect by Western blotting.

EXAMPLE 5

Expression of the Selected Marker Protein According to Cancer Stage

Total 143 stomach cancer patients (training group-100, evaluating group-43) were divided by stage (1-4) and expressions of 9 marker proteins were investigated according to the stage. Particularly, stomach cancer patient data were divided into 4 groups according to the stage (stage 1-53, stage 2-36, stage 3-34 and stage 4-20). Mean value of those 9 protein expressions was calculated for each group, which was divided by mean value of those 9 protein expressions in normal healthy 168 people (FIG. 3). The resultant numerical value higher than 1 indicates that the expressions of those marker proteins are increased in stomach cancer patients, while the numerical value lower than 1 indicates vise-versa. As a result, expressions of Leucine-rich alpha-2-glycoprotein (LRG), Clusterin, Alpha-1-antitrypsin, ProApolipoprotein A-I, Haptoglobin beta, Haptoglobin alpha-2 and Apolipoprotein H were increased in stomach cancer patients as the cancer progressed. In the meantime, expressions of Apolipoprotein A-IV and Transthyretin were reduced in stomach cancer patients as the cancer progressed. That is, those 9 marker protein expressions differ between normal and stomach cancer and according to the stage, indicating that these markers exhibit characteristic expression patterns, increase or decrease according to the cancer stage. In conclusion, markers for diagnosing stomach cancer screened above show different expression patterns between normal and stomach cancer status and according to the cancer stage.

INDUSTRIAL APPLICABILITY

The marker proteins for diagnosing stomach cancer of the present invention and a diagnostic kit using the same facilitate early diagnosis of stomach cancer simply by checking their expressions in body fluid and thereby facilitate quick response for the treatment. Therefore, it is expected that the marker proteins can contribute to improvement of survival rate of stomach cancer patients developed approximately at least 20,000 patients/year and to reduction of national health care costs by cancer treatment.

SEQUENCE LIST TEXT

SEQ. ID. NO: 1 is a polypeptide sequence of Leucine-rich alpha-2-glycoprotein (LRG).

SEQ. ID. NO: 2 is a polypeptide sequence of Clusterin.

SEQ. ID. NO: 3 is a polypeptide sequence of Alpha-1-antitrypsin.

SEQ. ID. NO: 4 is a polypeptide sequence of Apolipoprotein A-IV.

SEQ. ID. NO: 5 is a polypeptide sequence of Transthyretin (Prealbumin).

SEQ. ID. NO: 6 is a polypeptide sequence of ProApolipoprotein A-I.

SEQ. ID. NO: 7 is a polypeptide sequence of Haptoglobin beta.

SEQ. ID. NO: 8 is a polypeptide sequence of Haptoglobin alpha-2.

SEQ. ID. NO: 9 is a polypeptide sequence of Apolipoprotein H.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of diagnosing stomach cancer in a subject, comprising:
   determining an expression level of one or more proteins in a serum sample from the subject, wherein the proteins are selected from the group consisting of Leucine-rich alpha-2-glycoprotein (LRG), Clusterin, Apolipoprotein A-IV, Transthyretin, and ProApolipoprotein A-I;
   comparing the expression level of said one or more proteins to expression level of said one or more proteins in a normal control serum sample; and
   diagnosing, the subject with stomach cancer if there is an increase in expression level of one or more of LRG, Clusterin, and ProApolipoprotein A-I as compared to the control serum sample, a decrease in expression level of one or more of Apoliprotein A-IV and Transthyretin as compared to the control serum sample, or any combination thereof.

2. The method of claim 1, wherein the one or more proteins are used independently or one or more or all of the proteins are used together.

3. The method of claim 1, wherein the expression level of all of the proteins is determined, and an increase in the expression level of each of Leucine-rich alpha-2-glycoprotein (LRG), Clusterin, and ProApolipoprotein A-I, and a decrease in the expression level of each of Apolipoprotein A-IV and Transthyretin as compared with expression level in a normal control sample indicates the presence of stomach cancer.

4. A method of determining stomach cancer stage, comprising:
   determining an expression level of one or more proteins in a serum sample obtained from a patient having stomach cancer, wherein the protein is selected from the group consisting of Leucine-rich alpha-2-glycoprotein (LRG), Clusterin, Apolipoprotein A-IV, Transthyretin, and ProApolipoprotein A-I; and
   determining a ratio of expression of the one or more proteins in the serum sample from the patient and expression of the one or more proteins in a normal control serum sample; and
   determining the stomach cancer stage, wherein an increase in the ratio of expression of one or more of LRG, Clusterin, and ProApolipoprotein A-I, a decrease in the ratio of expression of one or more of Apoliprotein A-IV and Transthyretin, or any combination thereof indicates a higher stomach cancer stage.

5. The method of claim 4, wherein an increased ratio of expression of one or more of Leucine-rich alpha-2-glycoprotein (LRG), Clusterin, and ProApolipoprotein A-I indicates a higher stomach cancer stage.

6. The method of claim 4, wherein a decreased ratio of expression of one or more of Apolipoprotein A-IV and Transthyretin indicates a higher stomach cancer stage.

7. The method of claim 4, wherein the ratio of expression of each of the proteins selected from the group consisting of LRG, Clusterin, Apolipoprotein A-IV, Transthyretin and ProApolipoprotein A-I in the serum sample from the patient and in the normal control serum sample is determined, and wherein an increase in the ratio of expression of each of Leucine-rich alpha-2-glycoprotein (LRG), Clusterin, and ProApolipoprotein A-I, and a decrease in the ratio of expression of each of Apolipoprotein A-IV and Transthyretin indicates a higher stomach cancer stage.

* * * * *